(12) United States Patent
Hårdemark

(10) Patent No.: US 9,694,204 B2
(45) Date of Patent: Jul. 4, 2017

(54) METHOD AND SYSTEM FOR ROBUST RADIOTHERAPY TREATMENT PLANNING

(71) Applicant: RaySearch Laboratories AB, Stockholm (SE)

(72) Inventor: Björn Hårdemark, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 14/781,415

(22) PCT Filed: Dec. 2, 2013

(86) PCT No.: PCT/EP2013/075223
§ 371 (c)(1),
(2) Date: Sep. 30, 2015

(87) PCT Pub. No.: WO2014/191064
PCT Pub. Date: Dec. 4, 2014

(65) Prior Publication Data
US 2016/0051840 A1 Feb. 25, 2016

(30) Foreign Application Priority Data
May 31, 2013 (EP) .................................. 13170163

(51) Int. Cl.
*A61N 5/10* (2006.01)

(52) U.S. Cl.
CPC ......... *A61N 5/1031* (2013.01); *A61N 5/1038* (2013.01); *A61N 5/1039* (2013.01); *A61N 5/1045* (2013.01); *A61N 2005/1074* (2013.01)

(58) Field of Classification Search
CPC .... A61N 5/103; A61N 5/1031; A61N 5/1038; A61N 5/1039
See application file for complete search history.

(56) References Cited

U.S. PATENT DOCUMENTS

| 2009/0234626 | A1 | 9/2009 | Yu et al. | |
| 2010/0228116 | A1* | 9/2010 | Lu ..................... | A61N 5/103 600/411 |
| 2013/0102830 | A1* | 4/2013 | Otto .................... | A61N 5/1031 600/1 |

FOREIGN PATENT DOCUMENTS

| WO | WO-2009/055775 A2 | 4/2009 |
| WO | WO-2010/102068 A2 | 9/2010 |

OTHER PUBLICATIONS

International Search Report dated Jan. 31, 2014 in International Application No. PCT/EP2013/075223.

(Continued)

*Primary Examiner* — Charles A Marmor, II
*Assistant Examiner* — Thaddeus Cox
(74) *Attorney, Agent, or Firm* — Drinker Biddle & Reath LLP

(57) ABSTRACT

A method for generating a robust radiotherapy treatment plan for a treatment volume of a subject. An adjusted voxel-specific dose objective is determined by "smearing" an initial voxel-specific dose objective a specified distance in at least one direction. A treatment plan based on such adjusted dose objective will be more robust with respect to setup uncertainties and organ movements. Smearing of the dose objective corresponds to adjusting the dose objective dose value of a voxel in accordance with dose objective dose values of voxels within the specified distance.

10 Claims, 6 Drawing Sheets

(56) References Cited

OTHER PUBLICATIONS

Extended European Search Report dated Nov. 5, 2013 in European Patent Application No. 13170163.3.

* cited by examiner

METHOD AND SYSTEM FOR ROBUST RADIOTHERAPY TREATMENT PLANNING

CROSS REFERENCE TO RELATED APPLICATIONS

This application is a National Stage of International Application No. PCT/EP2013/075223 filed Dec. 2, 2013, which claims benefit of European Patent Application No. 13170163.3 filed May 31, 2013, both of which are herein incorporated by reference in their entirety.

The present invention relates to the field of radiotherapy, and in particular to radiotherapy treatment planning wherein a heterogeneous dose is prescribed to a region of interest.

BACKGROUND

In conventional planning of radiation treatments, a forward planning approach is commonly employed, in which the treatment planner manually alters treatment parameters until an acceptable dose distribution is obtained. For Intensity Modulated Radiation Therapy (IMRT), an inverse planning approach is usually employed where the treatment planner specifies requirements on the dose distribution, which are taken as input to an optimization algorithm trying to find the set of treatment parameters which most effectively produces the desired dose distributions.

The general procedures of inverse treatment planning, and the various steps involved when using a Treatment Planning System (TPS) for optimizing a treatment plan, are well-known to a person skilled in the art of radiotherapy treatment planning and details thereof are therefore not further described here.

When prescribing a radiation dose to a target, e.g. a tumor, a homogeneous dose is usually desired. However, under certain circumstances it would be advantageous to deliver a deliberately heterogeneous dose to a target volume or another Region Of Interest (ROI) such as an Organ At Risk (OAR). This would be desirable for example in the field of adaptive radiotherapy where a treatment plan is re-optimized during the course of treatment. Radiotherapy treatment is usually fractionated, i.e. the treatment time is extended, often over several weeks, where fractions of the total planned dose are administered daily. If the delivered dose of some fractions for any reason does not match the intended dose, some sub-regions of a ROI might become underdosed (having "cold spots") or overdosed (having "hot spots"). In this context, adaptive radiotherapy refers to the process of modifying a treatment plan in between fractions, in order to compensate for a delivered dose which deviates from the intended dose. Thus, when adapting the treatment plan, a deliberately inhomogeneous dose prescription, compensating for cold and/or hot spots, might be used as input to the treatment planning system.

Another case where prescribing a deliberately inhomogeneous dose is advantageous is when using functional imaging information, for example obtained from a PET-scan, as input to the TPS. Such functional imaging information could indicate regions within a target which are more or less radiosensitive, thus indicating that different doses should be delivered to different parts of the target.

Regardless if a homogeneous or a heterogeneous dose is prescribed to a target volume, a clinically useful treatment plan must take position uncertainties and organ motion into account. In order to do this, margins are often applied around a region of interest, such as a target volume, to ensure that the whole volume receives the intended dose. Such a margin when applied to a Clinical Target Volume (CTV) defines the Planning Target Volume (PTV). In order to limit the dose to healthy tissue as much as possible, the margin should not be larger than necessary. When planning delivery of a heterogeneous dose to a region, a margin around the region will not help to achieve a plan which is robust with respect to the different dose levels within the region.

Other methods for obtaining robust treatment plans, which do not depend on the use of margins but use a probabilistic approach, are also known in the art. Such methods often involve consideration of a number of more or less probable scenarios, for example defined by different shifts of the CTV. This kind of robust treatment planning is time-consuming and computationally intensive, since many different scenarios must be analyzed. Furthermore, such methods would be of limited use when planning delivery of a heterogeneous dose due to the large number of scenarios that would have to be taken into consideration.

The present invention aims at mitigating these drawbacks and achieving treatment planning of heterogeneous doses which is both computationally efficient and robust, i.e., insensitive to position uncertainties and organ movements.

Prescribing a heterogeneous dose implicates the use of a voxel-specific dose objective for the optimization of a treatment plan. As used herein, a voxel-specific dose objective is a dose objective for a volume comprising more than one voxel (volume element of the treatment volume), where the voxels of the volume have specific and possibly different dose objectives. In this regard, a prescribed heterogeneous dose corresponds to a voxel-specific dose objective defining different dose objective dose values for different voxels.

SUMMARY OF THE INVENTION

According to one aspect of the invention, a method for generating a robust treatment plan for a treatment volume of a subject (e.g. a patient) is provided, said treatment volume being defined using a plurality of voxels. Preferably, the method includes:
- retrieving an initial voxel-specific dose objective defining an initial dose objective dose value for each of a number of voxels in the treatment volume, the initial voxel-specific dose objective corresponding to a desired heterogeneous dose in said treatment volume;
- determining at least one adjusted dose objective dose value, for at least one voxel of the number of voxels, comprising performing the following steps a)-c):
  a) designating one voxel of said number of voxels, for which an adjusted dose objective dose value has not been obtained, as a current voxel for which the initial dose objective dose value is to be adjusted,
  b) identifying one or more reference voxels in said treatment volume, each of said one or more reference voxels being located within a distance from said designated current voxel,
  c) adjusting the initial dose objective dose value of said designated current voxel on the basis of the initial dose objective dose values of the one or more reference voxels, whereby an adjusted dose objective dose value of said current voxel is obtained;
- determining an adjusted voxel-specific dose objective for said treatment volume at least partly based on said at least one adjusted dose objective dose values;
- generating a radiation treatment plan at least partly on the basis of said adjusted voxel-specific dose objective.

According to another aspect of the invention, a computer program is provided. Preferably, the computer program comprises computer-readable instructions which, when executed on a computer, will cause the computer to perform the method for generating a robust treatment plan.

According to yet another aspect of the invention, a treatment planning system is provided. Preferably, the treatment planning system comprises a processor and at least one memory having stored thereon the computer program comprising the computer-readable instructions for generating a robust treatment plan, wherein the processor is coupled to the memory and configured to execute the computer-readable instructions.

The invention is based on the observation that in order to obtain a robust treatment plan when prescribing a heterogeneous dose, the dose objective itself could be adjusted by "smearing" the dose objective in accordance with a specified distance, hereunder sometimes referred to as a "smearing distance". Smearing of the dose objective corresponds to adjusting the dose objective of a voxel in accordance with dose objective dose values of other voxels within the specified smearing distance from the voxel. Preferably, the dose objective dose values of all voxels within a treatment volume, such as a region of interest (e.g. a PTV), are adjusted in a corresponding way. Such an adjusted dose objective will after optimization yield a robust treatment plan which is robust also with respect to different dose levels within a region of interest, irrespective of whether or not a margin has been applied.

According to some embodiments, an adjusted dose objective dose value of a current voxel corresponds to the maximum or minimum of the initial dose objective dose values of said reference voxels. Thus, the maximum prescribed dose found within the distance could be used as an adjusted minimum dose objective (and possibly also as maximum dose objective) for the voxel. Alternatively, the minimum prescribed dose value found within the distance could be used as an adjusted maximum dose objective for the voxel. Typically, the former approach would be used in a target region (e.g. in a PTV) and the latter in a risk organ (OAR). Hence, different methods could be used for adjusting voxel-specific dose objectives of different ROIs in a treatment volume.

According to some embodiments, the adjusted dose objective dose value of said first voxel is calculated using two or more of the initial dose objective dose values of said second voxels. Hence, as an alternative to using only the maximum or minimum dose objective dose value, the dose objective dose values of all, or a sub-set of, the voxels within the smearing distance could be used to determine the new dose objective, for example by calculating a mean or a quadratic mean of the dose objective dose values.

According to some embodiments, the distance in at least one direction is a predetermined constant distance.

According to some embodiments, where the treatment volume comprises a region of interest, said distance in at least one direction is based on the extent of a margin around the region of interest. This would for example be advantageous when smearing a heterogeneous dose prescribed to a CTV, since the extent of a user-defined PTV usually represents an approximation of the foreseen position uncertainties of the CTV. Hence, information already specified by a user could be re-utilized when smearing the dose prescribed to a CTV. Where a non-constant margin is used, the distance can correspond to the maximum extent of the margin, i.e. the distance between the region border and the corresponding margin border at the location where the margin is the largest. The smearing distance might be limited in some directions near the border of the region, so as to not extend beyond the margin (e.g. beyond the PTV border). Thereby, dose will not be prescribed outside the region where dose was originally prescribed.

According to some embodiments the distance can be different in different directions, i.e. the smearing of the dose objective does not have to be the same in all directions.

According to some embodiments, the extension of a non-constant margin in various directions can be used as basis for determining a varying smearing distance in different directions.

According to some embodiments, a user is allowed to specify and/or modify said distance in at least one direction. Thereby a user would be able to modify a pre-defined or margin-based smearing distance.

According to some embodiments, the desired heterogeneous dose corresponds to an adapted dose objective used for adaptive radiation treatment. Thereby, an adapted treatment plan, compensating for previous errors in dose delivery, would be robust.

According to some embodiments, said desired heterogeneous dose is determined partly on basis of functional imaging data indicating functional or biological tissue information. Thereby, a treatment plan based on functional information, for example a plan taking varying tissue radiosensitivity into account, would be robust.

Further aspects of the invention will become apparent by consideration of the detailed description and accompanying drawings. These are only for purposes of illustrating preferred embodiments and are not to be construed as limiting the invention.

DETAILED DESCRIPTION

Figure 1A:
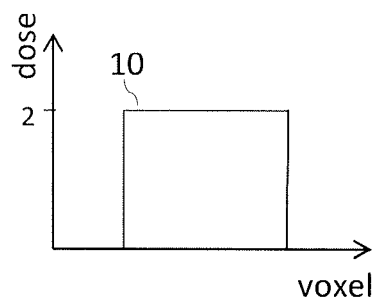
FIG. 1a shows an originally prescribed dose to voxels along a line through a target region.

FIG. 1a shows a prescribed fraction dose 10 to a clinical target volume (CTV) along a line through the CTV. The dose level is shown on the Y-axis, and the position within the target is shown on the X-axis. A minimum dose of 2 Gy is prescribed to all voxels.

In addition to, or instead of, using a minimum dose objective, other objectives could be used. For example, it would be possible to prescribe both a minimum dose objective and a maximum dose objective. In these cases, the maximum and minimum objectives could be differently weighted in the objective function used for the optimization, as will be described in more detail below.

During fractionated radiotherapy, a treatment plan may have to be adapted due to errors in the delivered dose of previous fractions. For example, such errors might be caused by misalignments between the radiation source and the patient, or as a result of changes of the shape or position of organs or tumors. The errors in delivered dose can for example be estimated from treatment images acquired at the time of treatment, for example using portal imaging or any other suitable 2D- or 3D-imaging modality such as CBCT, MVCT, Ultrasound or MRI. If a treatment image is acquired for a specific treatment session, the actually delivered fraction dose may be calculated by mapping the dose to the new geometry as determined from the treatment image. For example, as is well-known in the art, this can be achieved by deformably registering the treatment image with the planning image (the image on which the treatment planning was based) and deform the dose accordingly using the registration result. The actually delivered fraction doses may be accumulated and the total dose can therefore be monitored during the course of treatment.

Figure 1B:
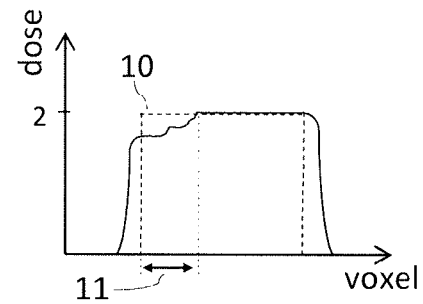
FIG. 1b shows the dose actually delivered.

FIG. 1b shows the dose to the target as actually delivered in the first fraction. The delivered dose deviates more than acceptable from the planned dose (the dose determined by treatment planning). The planned dose is not shown in the figures, but is in this example considered to substantially correspond to the prescribed dose 10 (indicated with a dashed line in FIG. 1b). Hence, in relation to the planned dose, there is a substantial cold spot 11 at the leftmost edge of the CTV. Either the prescribed dose or the planned dose could be used as reference when determining an initial heterogeneous dose objective, as described in more detail with reference to FIG. 1c.

Figure 1C:
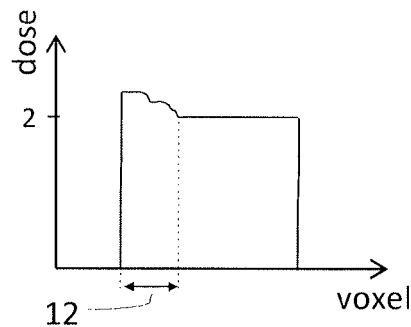
FIG. 1c shows a dose initially prescribed on basis of the discrepancy between the doses of FIGS. 1a and 1b.

To compensate for the cold spot 11, an adapted treatment plan for the second fraction can be determined, aiming at delivering the originally prescribed fraction dose and an additional "boost" to the cold spot. Hence, a deliberately heterogeneous dose is prescribed to compensate for the unintentionally heterogeneous dose previously delivered. FIG. 1c shows the initial (not yet adjusted) heterogeneous dose prescription for the second fraction, which takes the cold spot of the first fraction into consideration. The prescribed dose is composed of the originally prescribed 2 Gy and a "boost" to a region 12 corresponding to the cold spot 11. For example, the dose objective $d_{j2\_obj}$ to a voxel j for the second fraction may be determined from $d_{j2\_obj}=d_{f2}+(d_{f1}-d_{j1})$, where $d_{f2}$ is the originally prescribed dose for the second fraction, $d_{f1}$ is the prescribed dose of the first fraction and $d_{j1}$ is the actually delivered dose to voxel j in the first fraction. Using constant fraction doses ($d_{f2}=d_{f1}$), the prescribed dose objective to a voxel j for the second fraction would be $d_{j2\_obj}=2d_{f1}-d_{j1}$.

If the target has been deformed during the course of the treatment, the outlines of the CTV may have to be modified before prescribing the heterogeneous dose and adapting the treatment plan. However, using deformed and accumulated doses to voxels of the target as described previously, the dose errors of voxels in a deformed CTV can still be determined and a heterogeneous dose prescribed on basis thereof.

Figure 1D:
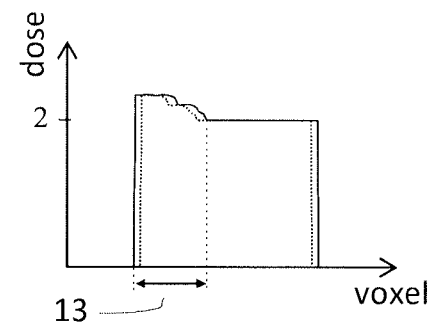
FIG. 1d shows the adjusted prescribed dose which is used for determining the treatment plan.

In FIG. 1d, the initially prescribed heterogeneous dose of FIG. 1c is indicated as a dashed line, whereas the solid line indicates the prescribed heterogeneous dose after being adjusted using the method according to the invention. The adjustment of the initially prescribed dose is achieved by "smearing" the corresponding voxel-specific dose objective, resulting in an extended dose boost region 13. The smearing according to the invention is described in more detail below with reference to FIG. 4.

Figure 2A:
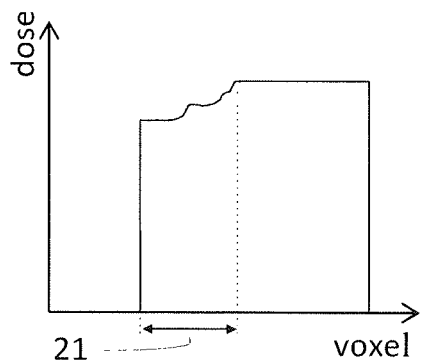
FIG. 2a shows an initially prescribed dose to voxels along a line through a risk organ.
Figure 2B:
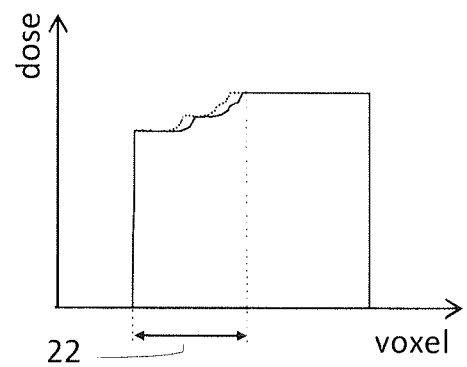
FIG. 2b shows the adjusted prescribed dose which is used for determining the treatment plan.

According to another example embodiment, illustrated in FIGS. 2a and 2b, a heterogeneous dose is prescribed to an organ at risk (OAR) defining maximum allowed doses to the voxels. Such a heterogeneous dose might be prescribed in order to specifically try to reduce the dose in certain parts of the OAR which have received a higher dose than allowed during previous fractions. FIG. 2a shows an initially prescribed heterogeneous dose along a line through an OAR where a reduced maximum allowed dose has been prescribed to a region 21 close to the OAR boundary. In FIG. 2b the dashed line indicates the initially prescribed heterogeneous dose of FIG. 2a and the solid line indicates the prescribed dose after being adjusted using the smearing procedure according to the invention (described below in more detail with reference to FIG. 5). The result is an increased region 22 of voxels having a reduced maximum dose objective. The adjusted dose objective will result in a more robust treatment plan where the prescribed lower allowed doses in region 21 with an increased probability will not be exceeded in any of the voxels.

Figure 3A:
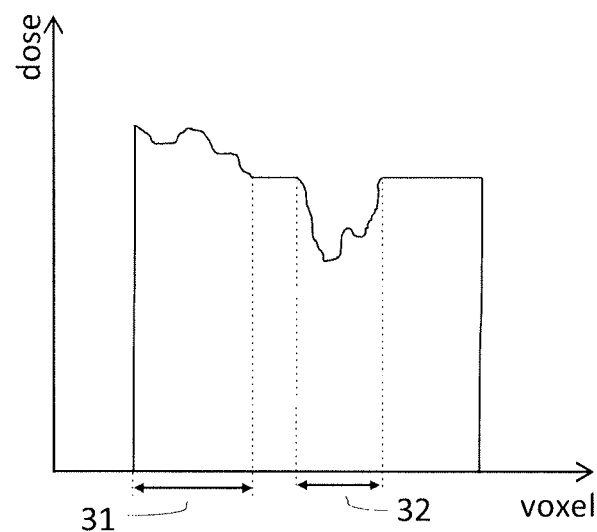
FIG. 3a shows an initially prescribed dose to voxels along a line through a target region and FIG. 3b shows the adjusted prescribed dose which is used for determining the treatment plan.
Figure 3B:
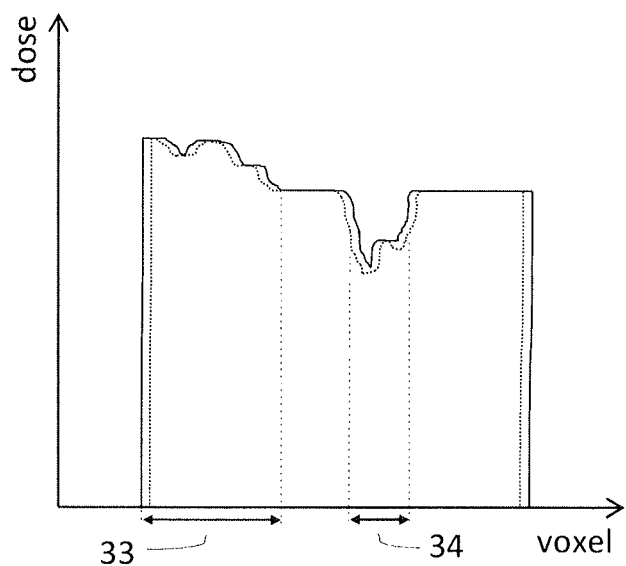

According to another example embodiment, illustrated in FIGS. 3a and 3b, an initial heterogeneous dose is prescribed in a target to compensate for both hot spots and cold spots resulting from errors in previous fractions. In order to obtain a more robust treatment plan, higher dose objectives are smeared using the method according to the invention (described in more detail below with reference to FIG. 4) to reduce the risk of under-dosing any voxels of the target. FIG. 3a shows a prescribed dose objective along a line through a CTV comprising a region 31 with increased prescribed dose and a region 32 with a reduced prescribed dose. In FIG. 3b the dashed line indicates the initially prescribed dose from FIG. 3a, whereas the solid line indicates the prescribed dose after being adjusted using the smearing procedure. As can be seen in FIG. 3b, the adjusted low-dose region 34 is narrowed, and the adjusted high-dose region 33 is extended, compared to the respective regions 32 and 31 in the initially prescribed dose.

The initial heterogeneous dose objectives according to the examples above are described in the context of adaptive radiotherapy. In other embodiments, initial heterogeneous dose objectives are prescribed on basis of functional or biological tissue information, for example describing varying radio-sensitivity of tissue within a region of interest. Such information could indicate that different dose levels should be prescribed to different voxels within the region. Functional information can for example be obtained from imaging based on PET, SPECT, perfusion CT or any other modality suitable for detecting functional or biological tissue information. Functionally based heterogeneous dose prescriptions might also be adapted during adaptive radiotherapy, as described above, and adjusted using the smearing method according to the invention.

The invention would be applicable in all situations where a deliberately heterogeneous dose is desired in a region to be irradiated.

Figure 4A:
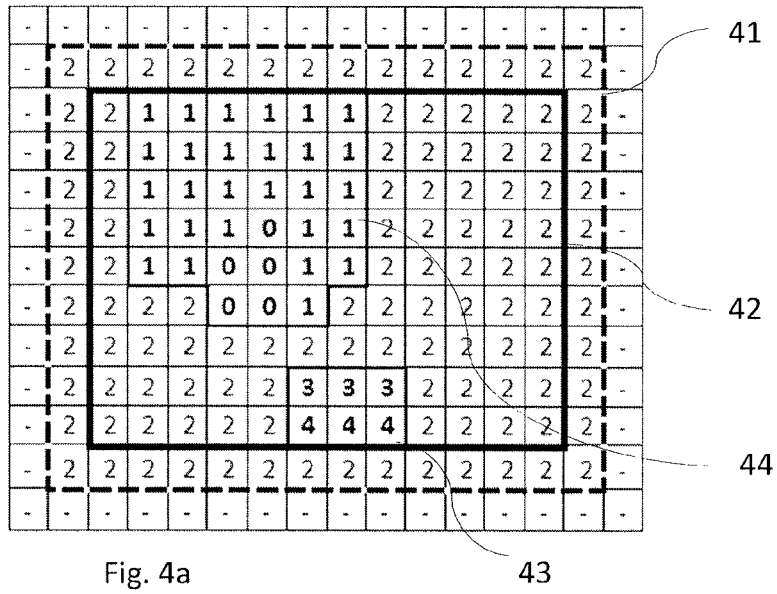
FIG. 4a shows a two-dimensional representation of an initially prescribed dose to voxels in a target region.
Figure 4B:
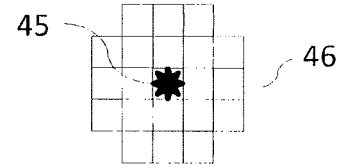
FIG. 4b shows a kernel defining the distance used for adjustment.
Figure 4C:
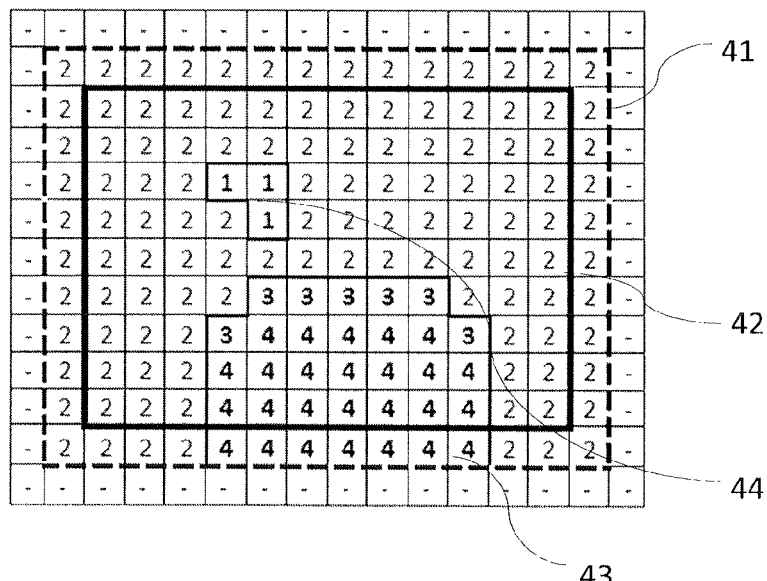
FIG. 4c shows the resulting adjusted prescribed dose.

FIGS. 4a, 4b and 4c illustrate a simplified example of dose objective smearing in two dimensions, i.e. in a single slice of the subject. As used herein, "smearing" of a dose objective corresponds to adjusting the dose objective dose value of a current voxel in accordance with dose objective dose values of other voxels within a specified "smearing distance" from the current voxel, sometimes defined by a "smearing kernel", as further described below.

FIG. 4a shows a clinical target volume (CTV) 42, of which the border is indicated by a solid line, and which has a rectangular cross-section of 9*12 voxels. A margin of one voxel's width is applied to the CTV, defining a planning target volume (PTV) 41 having a cross-section of 11*14 voxels, the border of which is indicated by a dashed line. An initial voxel-specific dose objective is indicated by specific dose objective dose values, ranging from 0 to 4 Gy, for each of the voxels within the PTV. In relation to an originally prescribed dose objective of 2 Gy, an increased dose is prescribed to voxels 43 in the lower part of the CTV and a reduced dose is prescribed to voxels 44 in the upper part of the CTV.

FIG. 4b shows a kernel 46, defined by a number of voxels, indicating the smearing distances in relation to a current voxel 45 of which the initial dose objective dose value is to be adjusted. The kernel of the present example is circle-like with a diameter corresponding to 5 voxels. In a full-scale example in three dimensions, a kernel defining a uniform smearing distance would preferably be sphere-like and consisting of a larger number of voxels. However, in the present two-dimensional example, the initial dose objective dose value of a current voxel 45 is adjusted by considering initial dose objective dose values of other voxels found within an area defined by the kernel 46 around the current voxel 45. The smearing, based on the kernel 46, is applied for adjusting the initial dose objective dose value of every voxel within the PTV. According to this example embodiment, the initial dose objective dose value of a current voxel to be modified is automatically changed to be the same as the initial dose objective dose value of the voxel within the kernel area which has the highest initial dose objective dose value. Other methods for adjusting a dose objective dose value are possible, as will be discussed in more detail below with reference to FIG. 8.

FIG. 4c shows the resulting adjusted dose objective where the prescribed high-dose region 43 is extended and the low-dose region 44 is narrowed. Thereby, the risk for not completely covering the region where an increased dose has been prescribed, and the risk for under-dosing voxels near the region where a lower dose has been prescribed, are reduced. In this example, initial dose objective dose values of all voxels within the PTV are modified. The dose smearing does not extend beyond the PTV and voxels outside the PTV are not considered when determining the adjusted dose objective dose values.

Figures 5A, 5B, 5C:
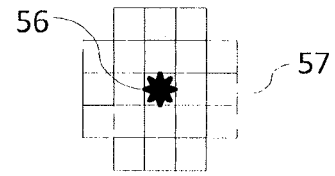
FIG. 5a shows a two-dimensional representation of an initially prescribed dose to a PTV and an overlapping OAR.
FIG. 5b shows a kernel defining the distance used for adjustment.
FIG. 5c shows the resulting adjusted prescribed dose.

In regions where a risk organ and a target, each having heterogeneous dose prescriptions to be smeared using the method according to the invention, are located close to each other or overlap, conflicts could occur due to smearing of different kinds of dose objectives into the same region. FIG. 5a illustrates a CTV 52, the border of which is indicated by a solid line, and a PTV 51, the border of which is indicated by a dashed line, overlapping an OAR 55, the border of which is indicated by another solid line. CTV 52 and OAR 55 have different prescribed heterogeneous dose objectives. More specifically, the OAR 55 has a region 54 with a reduced maximum dose objective and the CTV 52 has a region 53 with an increased minimum dose objective. FIG. 5b shows the smearing kernel 57 used, which is identical to, and has the same function as, the kernel described with reference to FIG. 4b. The smearing of the CTV dose objective is achieved in a way corresponding to the previous example illustrated by FIG. 4, resulting in an enlarged region 53 with an increased minimum dose objective. The smearing of the OAR dose objective is achieved by changing the initial dose objective dose value of a current voxel 56 to be the same as the initial dose objective dose value of the voxel within the kernel area which has the lowest initial dose objective dose value. The dose objective dose values of all voxels within the PTV and the OAR are adjusted accordingly. The smearing of the OAR dose objective results in an enlarged region 54 with a reduced maximum dose objective. The smearing is limited to not extend beyond the boundaries of the PTV 51 and the OAR 55. FIG. 5c shows the resulting adjusted dose objective after smearing. The resulting adjusted dose objective dose values in voxels 58 where conflicts arise indicate both the maximum dose objective (0) and the minimum dose objectives (2, 3). The result of a subsequent optimization of such conflicting dose objectives will depend on how the minimum dose objective is weighted in relation to the maximum dose objective (i.e. whether covering the target region or sparing the risk organ is considered more important).

It should be emphasized that an optimization will usually include additional treatment objectives or constraints relating to the illustrated ROIs and/or to other regions. All the objectives and constraints will affect the optimization of the treatment plan.

Figure 6:
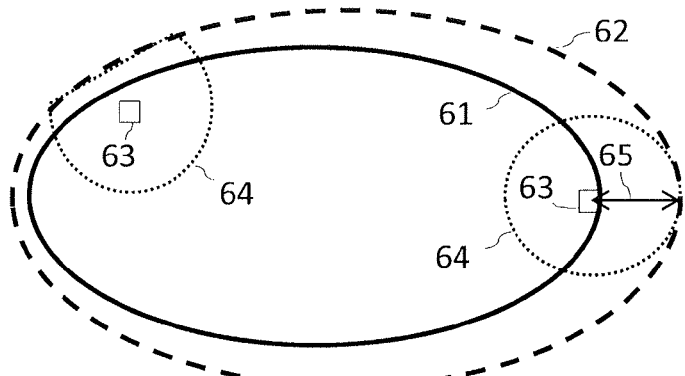
FIG. 6 shows a representation of a target region and how the distance used for dose adjustment is determined based on the extent of a PTV margin.

According to some embodiments, the smearing distance is based on the margin of a ROI. Hence, for example, the smearing distance could be automatically set as the distance between a CTV boundary and a corresponding PTV boundary. This is advantageous since the extent of a user-defined PTV usually represents an approximation of the position uncertainties of the CTV, and therefore corresponds to a suitable smearing distance of a dose prescribed to the CTV. Even when a non-uniform margin is used, automatic determination of a smearing distance based on the margin is possible. FIG. 6 shows a cross-sectional view of a CTV 61 and a corresponding PTV 62, of which the border is indicated by a dashed line. As seen in the figure, the PTV margin is non-constant. The smearing distance used for adjusting a prescribed heterogeneous CTV dose corresponds to the largest distance 65 between the CTV 61 and the PTV 62. Smearing distances in relation to voxels within the PTV are indicated by schematically illustrated smearing kernels 64 around voxels 63. Hence, in this example, the smearing distance is limited in directions wherever the adjusted dose objective otherwise would extend outside the PTV. Thus, the extension of the dose smearing kernel is limited in certain directions near the PTV border and only dose objective dose values of voxels within the PTV are adjusted.

Figure 7A:
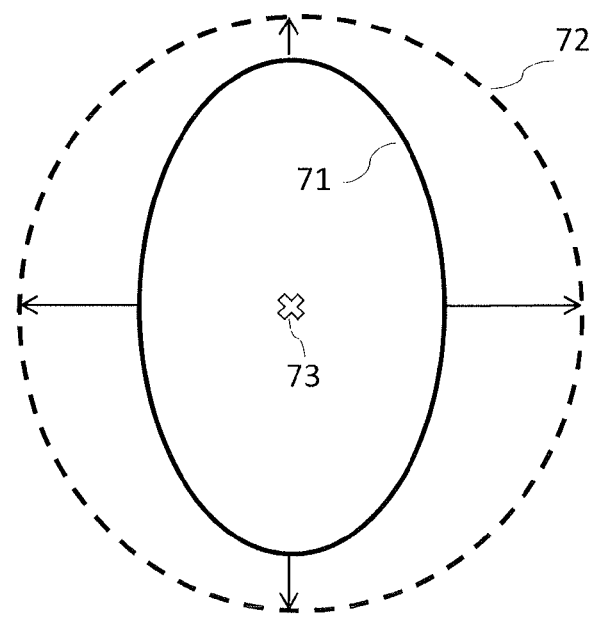
FIG. 7a shows a target region and FIG. 7b shows a corresponding non-uniform kernel defining the distance used for adjustment.
Figure 7B:
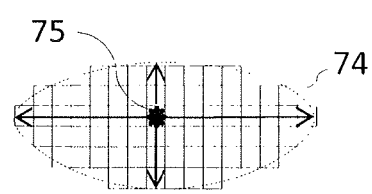

Instead of using a constant distance, the smearing distance could vary in different directions, for example based on the extent of the margin in said directions. Thus, if a PTV margin which is more extensive along a specific direction indicates that CTV motion is more likely along this direction, the dose objective could be smeared further in this direction. More specifically, the smearing kernel used could depend on the margin extension in different directions. FIG. 7a shows a cross-sectional view of a CTV 71 and a PTV 72, where the non-uniform margin is indicative of an increased position uncertainty along the horizontal direction. FIG. 7b shows a dose smearing kernel 74, in relation to a current voxel 75 of which the dose objective dose value is to be adjusted, where the extension of the kernel is based on the extension of the PTV margin in four directions in relation to the CTV centroid 73, as indicated by arrows in FIGS. 7a and 7b. The kernel 74 functions in a corresponding way as the kernels described previously with reference to FIGS. 4b and 5b. Other methods can be used for determining appropriate dose smearing kernels based on non-constant margins. For example, various iterative methods for optimizing the extension of a smearing kernel in different directions are possible. It is also possible to employ voxel-specific smearing kernels, i.e., smearing kernels that are different for different voxels within a region.

The rationale for selecting a smearing distance based on a margin extension is the observation that a user-defined margin (e.g. a PTV) can indicate the extent of expected position uncertainties of the target in different directions. Generally, a large margin could indicate substantial position uncertainties. If a larger margin is defined only along a specific direction, this could indicate that the position uncertainties are greater along this direction, e.g. because of an increased freedom of movement compared to other directions. Therefore, in such cases, it would be advantageous to also smear the dose objective further in the corresponding directions. Non-constant margins can be applied to a region for other reasons, for example to reduce the risk of exceeding an allowed dose within an OAR located nearby. Hence, additional information, for example input from a user, might be needed to decide whether or not a non-constant margin should be used for defining varying smearing distances in different directions.

The idea of estimating position uncertainties of a region on the basis of the extension of a margin in different directions can be utilized in other applications and are not limited to the dose smearing method described herein. Hence, more generally, a method is described for estimating position uncertainties of a region on basis of the extension of a margin around the region in a plurality of directions, wherein the estimated uncertainties could be used as input for any treatment planning related method, such as, for example, robust treatment planning as referred to in the background section.

Figure 8:
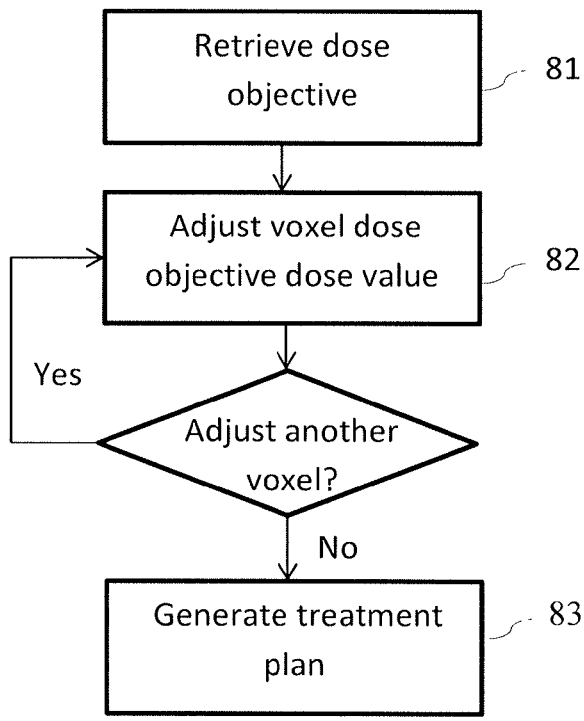
FIG. 8 is a flowchart indicating the steps of a method according to the invention.

FIG. 8 is a flowchart showing the steps of a method according to the invention. In the first step 81, a dose objective defining a desired heterogeneous dose in a treatment volume, such as in one or more regions of interest, is retrieved. The treatment volume is defined using a grid of voxels and the desired heterogeneous dose is represented by an initial voxel-specific dose objective defining specific initial dose objective dose values for different voxels in the treatment volume.

Thereafter, in step 82, the initial dose objective dose value of a voxel is adjusted by considering initial dose objective dose values of other voxels (reference voxels) within a specified smearing distance in various directions, e.g. as defined by a smearing kernel such as, for example, any of the kernels illustrated in FIG. 4b, 5b or 7b.

An adjusted dose objective dose value of a voxel can be obtained by replacing the initial value with a maximum and/or minimum dose objective dose value found within the smearing kernel, as described above with reference to FIGS. 4c and 5c. Alternatively, an adjusted dose objective dose value of a voxel could be determined in other ways. For example, an average, or a weighted average, of all dose objective dose values within a smearing kernel could be used as an adjusted dose objective dose value for a voxel. Alternatively, the quadratic mean (root mean square) could be used, i.e. the square root of the mean of the squares of the values. Various other possibilities for determining an adjusted dose objective dose value based on dose objective dose values in nearby voxels are envisaged. For example, only a subset of the voxels within the distance might be analyzed, selected based on different criteria, or the most frequently occurring dose objective dose value or values could be selected. The invention shall not be considered as limited to any of these examples as many other methods are possible for achieving the dose smearing.

In any of the embodiments described, the smearing distance could be a predetermined value. Alternatively or additionally, the distance could be manually chosen or modified by a user. If the smearing distance is a predetermined value or automatically determined, for example based on a margin as described previously, the smearing of the dose objective is preferably a completely automatic process not requiring any user input. However, the TPS could also have a user interface for allowing specification or modification of smearing distances. Such user interface might be a graphical user interface allowing a user to directly indicate smearing distances in a 2D- or 3D-representation of a treatment volume. Alternatively or additionally, the user interface might allow a user to input numerical values of smearing distances in different directions, based upon which a smearing kernel can be determined.

By adjusting the initial dose objective dose value of a voxel, an adjusted voxel-specific dose objective is obtained. The step of adjusting an initial dose objective dose value of a voxel is preferably carried out for a plurality of voxels in the treatment volume, and most preferred for all voxels within the treatment volume. When a final adjusted voxel-specific dose objective has been determined, a treatment plan is generated in step 83.

In order to generate a treatment plan, treatment parameters are optimized by the treatment planning system, e.g. using inverse treatment planning. The treatment plan can be optimized for use in any kind of radiation treatment apparatus using any kind of modality including photons, protons or electrons. The treatment plan can be an Intensity Modulated Radiation Therapy (IMRT) plan or any other radiation treatment plan, such as, for example, a Three-Dimensional Conformal Radiation Therapy (3DCRT) plan or a Volumetric Modulated Arc Therapy (VMAT) plan.

A common approach in inverse treatment planning is to minimize (or maximize) an objective function composed of all optimization functions, often subject to certain planning constraints. The objective function can be a weighted sum of all optimization functions $f_i$, i.e., $$f = \sum_i w_i f_i \qquad (1)$$

where the weights $w_i$ of the optimization functions corresponds to the rates at which a decrease in one optimization function value is traded for an increase in a second optimization function value relating to another, possibly conflicting, treatment goal. It is possible to use voxel-specific weights reflecting the relative importance of the dose objectives of different voxels in a ROI.

A simple example of an optimization function $f_i$ relating to a voxel-specific dose objective of a ROI comprising j voxels, is:

$$f_i = \sum_j \Delta v_j \left( \frac{d_j - d_{j\_obj}}{d_{j\_obj}} \right)^2 \quad (2)$$

where $d_j$ is the dose in voxel j, $d_{j\_obj}$ is the (adjusted) dose objective dose value of voxel j, and $\Delta v_j$ is the relative volume of voxel j in the ROI. The dose $d_j$ is a function of the treatment parameters which are to be determined by the optimization. The normalization by multiplying with the relative volume and dividing by the square of the dose objective has the effect that, disregarding objective weights, all ROIs are considered to be equally important irrespective of volume and dose objective level.

Using an optimization function as defined in (2), both under- and overdosage with respect to the dose objectives are equally penalized. This is only an example and many other optimization functions can be employed instead of, or in addition to, this function. For example, radiobiologically based optimization functions can be used.

Various different optimization techniques may be employed when optimizing the objective function to arrive at a treatment plan. For example, gradient-based methods, such as methods based on sequential quadratic programming algorithms, or heuristic methods, such as simulated annealing, can be used. The optimization might be fluence-based, which requires subsequent conversion to machine parameters, or based on Direct Machine Parameter Optimization (DMPO) where machine parameters are directly optimized. As already mentioned, inverse treatment planning using optimization is well-known in the art.

Figure 9:
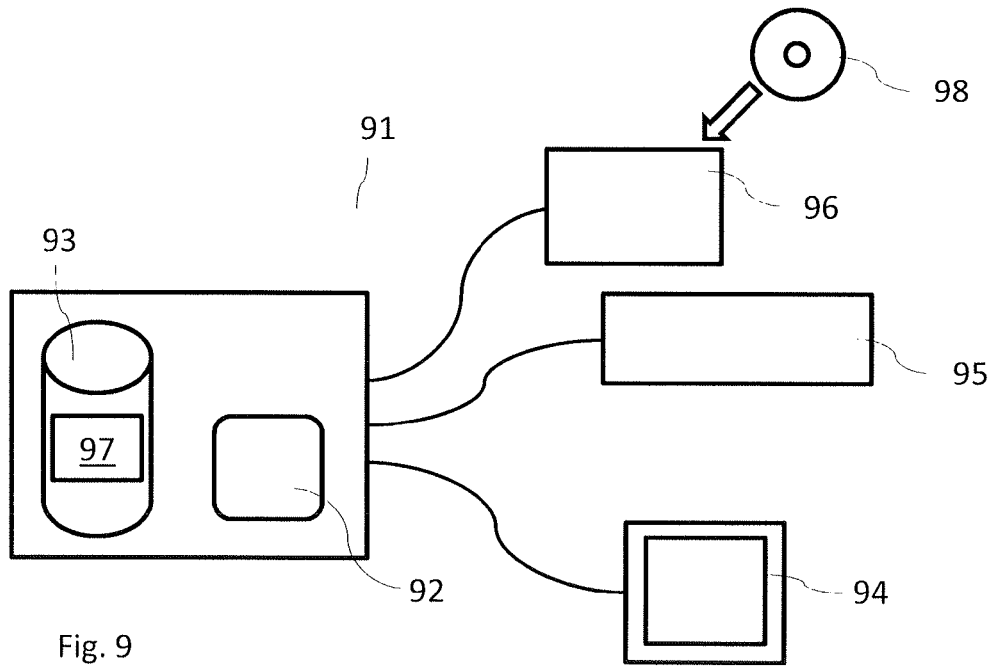
FIG. 9 schematically illustrates a treatment planning system according to the invention.

FIG. 9 schematically illustrates an example of a treatment planning system 91 according to the invention. The system comprises a processor 92, coupled to a memory 93. Furthermore, the system can include a display device 94 (e.g. for displaying various treatment planning related information, representations of a subject and treatment volumes, a graphical user interface, etc.), a data input device 95 (e.g. a keyboard, a mouse or any other suitable device for data input) and a data reading/writing device 96 (e.g. an optical drive, USB interface, or any other suitable device for reading/writing data). The processor 92 can be of any kind, such as, for example, one or more central processing units (CPU) or any kind of parallel processor system, e.g. based on one or more graphics processing units (GPU), or a combination thereof. The memory 93 can be any kind of volatile or non-volatile memory suitable for storing and retrieving information, such as, for example, a hard drive. The memory 93 has a computer program 97 stored thereon. The computer program 97 comprises computer-readable instructions for generating a robust treatment plan, where the computer-readable instructions can be transferred to, and executed by, the processor 92. When executed by the processor 92, the computer-readable instructions will perform a method as illustrated in FIG. 8 for generating a robust treatment plan, where an initial voxel-specific dose objective is retrieved, for example from memory 93, and an adjusted voxel-specific dose objective is calculated and a treatment plan is generated based on the adjusted voxel-specific dose objective. The adjusted voxel-specific dose objective and/or the generated treatment plan might be stored on the memory 93. The computer program 97 can also be stored on a non-transitory computer readable medium 98, e.g. a USB drive, an optical data carrier such as a CD-ROM, or any other suitable portable information storage device, so that the computer program 97 can be loaded to the memory 93 and/or transferred to different computing systems. The system described with reference to FIG. 9 is merely an example, and a treatment planning system according to the invention does not necessarily comprise all the illustrated components, and/or might comprise other components not illustrated.

The invention has been described with reference to a number of example embodiments. It is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for generating a robust radiation treatment plan for a treatment volume of a subject, said treatment volume being defined using a plurality of voxels, the method comprising, at a processor:
   retrieving an initial voxel-specific dose objective defining an initial dose objective dose value for each of a number of voxels in the treatment volume, the initial voxel-specific dose objective corresponding to a desired heterogeneous dose in said treatment volume;
   retrieving a distance corresponding to a desired robustness;
   determining an adjusted dose objective dose value for a voxel of the number of voxels, comprising performing the following steps a)-c):
   a) designating one voxel of said number of voxels, for which an adjusted dose objective dose value has not been obtained, as a current voxel for which the initial dose objective dose value is to be adjusted,
   b) identifying one or more reference voxels in said treatment volume, each of said one or more reference voxels being located within the distance in at least one direction from said designated current voxel, and
   c) adjusting the initial dose objective dose value of said designated current voxel on the basis of the initial dose objective dose values of the one or more reference voxels, whereby an adjusted dose objective dose value of said current voxel is obtained;
   repeating steps a)-c) to determine adjusted dose objective dose values for each of the plurality of voxels of the treatment volume;
   determining an adjusted voxel-specific dose objective for said treatment volume at least partly based on said adjusted dose objective dose values; and
   generating a radiation treatment plan at least partly on the basis of said adjusted voxel-specific dose objective.

2. A method according to claim 1, wherein the adjusted dose objective dose value of said current voxel corresponds to the maximum or minimum of the initial dose objective dose values of said one or more reference voxels.

3. A method according to claim 1, wherein the adjusted dose objective dose value of said current voxel is calculated using two or more of the initial dose objective dose values of said one or more reference voxels.

4. A method according to claim 1, wherein said treatment volume comprises a Region of Interest and said distance in at least one direction is based on the extent of a margin around said Region of Interest.

5. A method according to claim 1, wherein a user specifies and/or modifies said distance in at least one direction.

6. A method according to claim 1, wherein said desired heterogeneous dose corresponds to an adapted dose objective used for adaptive radiation treatment.

7. A method according to claim 1, wherein said desired heterogeneous dose is determined based on functional imaging data indicating functional or biological tissue information.

8. A computer program comprising computer-readable instructions which, when executed by a processor of a computer of a treatment planning system, will cause the computer to perform a method according to claim 1.

9. A computer program according to claim 8, wherein the computer-readable instructions comprise instructions for generating a user interface allowing a user to specify and/or modify said specified distance in at least one direction.

10. A treatment planning system comprising a processor and at least one memory having the computer program according to claim 8 stored thereon, wherein the processor is coupled to the memory and configured to execute the computer-readable instructions of the computer program.

* * * * *